United States Patent [19]

Giannessi et al.

[11] Patent Number: 5,491,260
[45] Date of Patent: Feb. 13, 1996

[54] PROCESS FOR MANUFACTURING L-(-)-CARNITINE FROM DERIVATIVES HAVING A CONFIGURATION OPPOSITE TO THAT OF L-(-)-CARNITINE

[75] Inventors: Fabio Giannessi, Rome; Roberto Castagnani, Recanati; Maria O. Tinti, Rome; Francesco De Angelis, Rome; Paolo De Witt, Rome; Domenico Misiti, Rome, all of Italy

[73] Assignee: Sigma-Tau Industrie Farmaceutiche Riunite S.p.A., Rome, Italy

[21] Appl. No.: 224,522

[22] Filed: Apr. 7, 1994

[30] Foreign Application Priority Data

Apr. 8, 1993 [IT] Italy ................... RM93A0226

[51] Int. Cl.⁶ .............. C07C 227/18; C07C 253/34; C07D 305/12
[52] U.S. Cl. .............. 562/567; 549/328; 560/227; 558/48; 558/50; 558/444
[58] Field of Search ............... 558/444, 48, 50; 549/328; 562/567; 560/227

[56] References Cited

U.S. PATENT DOCUMENTS

| | | | |
|---|---|---|---|
| 4,254,053 | 3/1981 | deWitt et al. | 564/198 X |
| 5,041,643 | 8/1991 | Tinti et al. | |
| 5,200,526 | 4/1993 | Arnold et al. | 548/375.1 |
| 5,412,113 | 5/1995 | Giannessi et al. | 549/328 |

FOREIGN PATENT DOCUMENTS

| | | |
|---|---|---|
| 0121444 | 10/1984 | European Pat. Off. |
| 0122794 | 10/1984 | European Pat. Off. |
| 0195944 | 10/1986 | European Pat. Off. |
| 0148132 | 9/1989 | European Pat. Off. |
| 0410430 | 1/1991 | European Pat. Off. |
| 0457735 | 11/1991 | European Pat. Off. |

OTHER PUBLICATIONS

Abstract only considered of JP62044189, Seitetsu Chem. Ind., Date Feb. 1987.
Abstract only considered of JP61271996, Seitetsu Chem. Ind., Date Dec. 1986.
Abstract only considered of JP61271995, Seitetsu Chem. Ind., Date Dec. 1986.
Abstract only considered of JP61234794, Seitetsu Chem. Ind. Date Oct. 1986.
Abstract only considered of JP61234788, Seitetsu Chem. Ind. Date Oct. 1986.
Abstract only considered of JP61067494, Seitetsu Chem. Ind., Date Apr. 1986.
Claims only considered of JP275689, Kabushiki, et al. Date Nov. 1987.
Hackh's Chemical Dictionary–4th Ed.–1969, pp. 437, 514, 645, 648.
Kirk–Othmer, Encyclopedia of Chemical Technology, 3rd ed., vol. 19 (1982), pp. 521–531.

*Primary Examiner*—Joseph Paul Brust
*Attorney, Agent, or Firm*—Oblon, Spivak, McClelland, Maier & Neustadt

[57] ABSTRACT

A Process for Preparing L-(–)-carnitine is disclosed which comprises acylating D-(+)-carnitinenitrile or D-(+)-carnitineamide to their respective acyl derivatives which, via acid hydrolysis, yield D-(+)-carnitine which is converted to the lactone of L-(–)-carnitine. The lactone when in base yields L-(–)-carnitine.

19 Claims, No Drawings

PROCESS FOR MANUFACTURING L-(-)-CARNITINE FROM DERIVATIVES HAVING A CONFIGURATION OPPOSITE TO THAT OF L-(-)-CARNITINE

BACKGROUND OF THE INVENTION

1. Field of the Invention

The present invention relates to an improved process for manufacturing L-(−)-carnitine from starting compounds containing an asymmetrical carbon atom having a configuration opposite to that of L-(−)-carnitine. The process of the present invention overcomes the drawbacks of conventional processes which first convert a starting compound into an achiral intermediate, generally crotonobetaine or gamma-butyrobetaine, and then convert the achiral intermediate to L-(−)-carnitine. The process of the present invention uses D-(+)-carnitinamide or D-(+)-carnitinenitrile as preferred starting compounds.

2. Discussion of the Background

Carnitine contains a single center of asymmetry and therefore exists as two enantiomers, designated D-(+)-carnitine and L-(−)-carnitine. Of these, only L-(−)-carnitine is found in living organisms, where it functions as a vehicle for transporting fatty acids across mitochondrial membranes. Whilst L-(−)-carnitine is the physiologically-active enantiomer, racemic D,L-carnitine has conventionally been used as a therapeutic agent. It is now recognized, however, that D-(+)-carnitine is a competitive inhibitor of carnitine acyltransferases, and that it diminishes the level of L-(−)-carnitine in myocardium and skeletal muscle.

It is therefore essential that only L-(−)-carnitine be administered to patients undergoing haemodialysis treatment or treatment for cardiac or lipid metabolism disorders. The same requirement applies to the therapeutic utilization of acyl derivatives of carnitine for treating disorders of the cerebral metabolism, peripheral neuropathies, peripheral vascular diseases and the like. These disorders are typically treated with acetyl L-(−)-carnitine and propionyl L-(−)-carnitine, which are obtained by acylating L-(−)-carnitine.

Various chemical procedures have been proposed for the industrial-scale production of carnitine. Unfortunately, these procedures are not stereospecific and produce racemic mixtures of D-(−)- and L-(−)-isomers. It is thus necessary to apply resolution methods in order to separate the enantiomeric constituents of the racemate.

Typically, the D,L-racemic mixture is reacted with an optically active acid (e.g. D-(−)-tartaric acid, D-(+)-camphorsulfonic acid, (+)-dibenzoyl-D-(−)-tartaric acid, N-acetyl-L-(+)-glutamic acid and D-(−)-camphoric acid) to obtain two diastereoisomers which can be separated from each other. In the classic process disclosed in U.S. Pat. No. 4,254,053, D-(−)-camphoric acid is used as the resolution agent of a racemic mixture of D,L-carnitinamide, obtaining D-(+)-carnitinamide as a by-product, and L-(−)-carnitinamide which, by hydrolysis, gives L-(−)-carnitine.

However, these resolution procedures are complex and costly, and in all cases result in the production of equimolar quantities of L-(−)-carnitine and D-(+)-carnitine or a precursor thereof as by-product, having configuration opposite to that of L-(−)-carnitine. Several microbiological processes have recently been proposed for producing L-(−)-carnitine via stereospecific transformation of achiral derivatives obtained from the huge amounts of D-(+)-carnitine (or of a precursor thereof, such as D-(+)-carnitinamide) which are generated as by-products in the industrial production of L-(−)-carnitine.

These processes are generally predicated upon the stereospecific hydration of crotonobetaine to L-(−)-carnitine, and differ principally by virtue of the particular microorganism employed to accomplish the biotransformation of interest. See, for example, the processes disclosed in: EP 0 12 1444 (HAMARI), EP 0 122 794 (AJINOMOTO), EP 0 148 132 (SIGMA-TAU), JP 275689/87 (BIORU), JP 61067494 (SEITETSU), JP 61234794 (SEITETSU), JP 61234788 (SEITETSU), JP 61271996 (SEITETSU), JP 61271995 (SEITETSU), EP 0 410 430 (LONZA), EP 0 195 914 (LONZA), EP 0 158 194 (LONZA), and EP 0 457 735 (SIGMA-TAU).

On the other hand, JP 62044189 (SEITETSU) discloses a process for stereoselectively producing L-(−)-carnitine starting from gamma-butyrobetaine, which is in turn obtained enzymatically from crotonbetaine.

All of these processes have several drawbacks. First, D-(+)-carnitine must first be converted to an achiral compound (crotonobetaine, gamma-butyrobetaine) before it can be used as the starting compound in all of the aforesaid microbiological processes.

In addition, the microbiological procedures proposed to date have not proven practicable for manufacturing L-(−)-carnitine on an industrial scale for one or more of the following reasons:

(i) the yield of L-(−)-carnitine is extremely low;

(ii) the microorganisms must be cultivated in a costly nutritive medium;

(iii) the microorganism can only tolerate low concentrations [up to 2–3% (w/v)] of crotonobetaine;

(iv) side reactions occur, such as the reduction of crotonobetaine to gamma-butyrobetaine or the oxidation of L-—carnitine to 3-dehydrocarnitine.

These side reactions reduce the final yield of L-(−)-carnitine.

In order to overcome all of the aforesaid drawbacks of the known processes, in the Italian patent application RM 92 A 000 915 filed on Dec. 21, 1992 in the name of the same applicants as the present application, not available to the public inspection at the filing date of this application, a process has been disclosed which allows high yields of L-(−)-carnitine to be obtained starting from a by-product having configuration opposite to that of L-(−)-carnitine (such as D-(+)-carnitinamide) with no need to first convert the starting by-product into an achiral intermediate.

This process which is illustrated in the following reaction scheme 1:

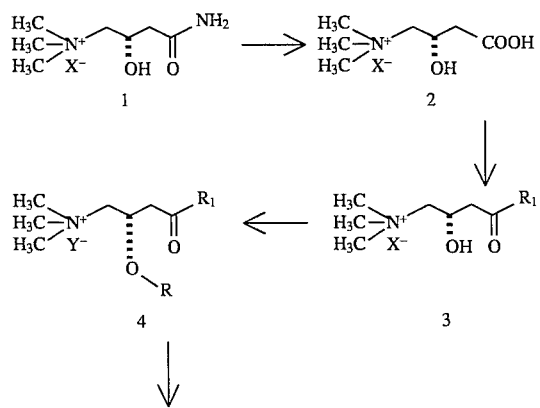

-continued
SCHEME 1

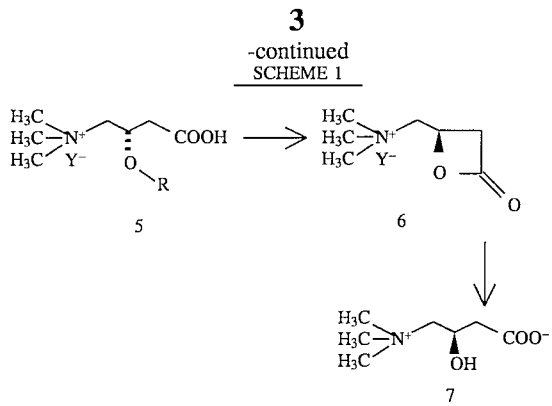

comprises hydrolyzing a D-(+)-carnitinamide salt 1 to D-(+)-carnitine 2 and esterifying 2 into ester 3 (via known methods) wherein R1 is preferably arylalkoxy, e.g. benzyloxy.

L-(−)-carnitine can suitably be purified from the salts which are formed from the $X^-$ anion, from the excess, if any, of the acyl halogenide, from pyridine, and the like, by chromatographing the aqueous solution on a strongly acidic resin such as IR 120, eluting with water and then with $NH_4OH$, or alternatively eluting first on a strongly basic resin such as AMBERLITE IRA 402 activated in OH form and thereafter on a weakly acid resin such as AMBERLITE IRC-50.

The process of the present invention which is illustrated in the following reaction scheme 2 constitutes a remarkable improvement over the previous process.

SCHEME 2

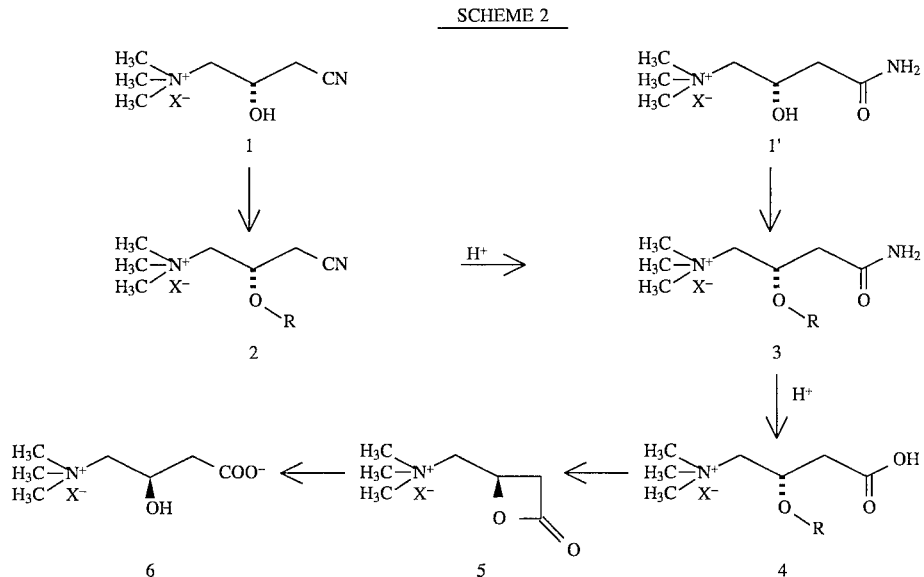

The ester 3 is then converted to the acyl derivative 4 wherein Y, which can be the same as X, is preferably a counterion, e.g. perchlorate, imparting solubility to 4. OR is a leaving group wherein R is preferably an alkylsulfonyl group having 1–12 carbon atoms, e.g. mesyl.

The acylation of 3 to 4 is carried out preferably in pyridine by reacting the ester 3 with an acylating agent RY wherein Y is halogen and R is an acyl group as defined above. Preferably RY is the chloride of the selected acyl group.

The ester group $-COR_1$ of 4 ($R_1$=benzyloxy) is hydrogenated to carboxyl group thus giving acyl D-(+)-carnitine 5 which is converted to the lactone 6 of L-(−)-carnitine. The lactonization is suitably carried out in an aqueous basic environment: either with $NaHCO_3$ (ratio 1:1) or with an AMBERLITE IRA-402 basic resin activated in $HCO_3^-$ form or with an LA2 resin. The lactone is isolated by evaporating the aqueous solution or precipitating it as a salt (for example, as tetraphenylborate or reineckate).

Finally, lactone 6 is suitably converted to L-(−)-carnitine inner salt 7. The lactone is dissolved in water and the resulting solution treated with a base such as $NaHCO_3$ (ratio 1:1), for 8–24 hours.

With reference to the reaction scheme 2; D-(+)-carnitinenitrile 1 wherein $X_{31}$ is any anion, preferably an anion imparting solubility, such as perchlorate, tetraphenylborate, alkylsulphonate wherein the alkyl group has 1–12 carbon atoms, is converted to acyl derivative 2 wherein OR is a good leaving group.

To this end, the acylation of 1 to 2 is carried out by reacting 1 with an acylating agent selected from RY wherein Y is halogen (e.g. chlorine) and the anhydride $R_2O$ wherein R is an alkyl- or arylsulfonyl or fluoroalkylsulfonyl group having 1–12 carbon atoms, formyl or trifluoroacetyl. Preferably, the alkylsulfonyl group is selected from methanesulfonyl (mesyl), p-toluenesulfonyl (tosyl), p-bromobenzenesulfonyl (brosyl), p-nitrobenzenesulfonyl (nosyl), trifluoromethanesulfonyl (triflyl), nonafluorobutanesulfonyl (nonaflyl) and 2,2,2-trifluoroethanesulfonyl (tresyl). Mesyl is particularly preferred.

When RY is a chloride, the reaction takes place in pyridine or pyridine alkyl derivatives wherein the alkyl group is lower alkyl having 1–4 carbon atoms, or in other basic organic solvents such as triethylamine, or in inert anhydrous organic solvents such as acetonitrile or methylene chloride, in mixture with a base such as pyridine, lutidine, picoline or polyvinylpyridine.

The acylating agent is added at ratios ranging from 1:1 to 1:10, preferably 1:3. The resulting reaction mixture is kept under stirring at 0° C.-50° C., for 1–24 hours.

The acyl D-(+)-carnitinenitrile 2 is converted via acid hydrolysis with conventional procedures to acyl D-(+)-carnitinamide 3 which can be directly arrived at by acylating D-(+)-carnitinamide with RY (as shown in the reaction scheme).

Hydrolysis of 2 takes place in an acid aqueous environment, at pH 0–4, at 50° C.–80° C., for 10–48 hours, yielding the intermediate acyl D-(+)-carnitinamide 3 which forms acyl D-(+)-carnitine 4.

The acyl D-(+)-carnitinamide 3 is hydrolyzed to acyl D-(+)-carnitine 4 under the same conditions.

Conversion of acyl D-(+)-carnitine 4 to lactone 5 and the conversion of this latter compound to L-(−)-carnitine 6 are carried out as disclosed in the previously cited Italian patent application RM92A000915.

It should be understood that, whereas the process disclosed above has been described, for the sake of clarity, as a sequence of four distinct operating steps, the corresponding industrial process consists of two steps only. When the process of the present invention is carried out as an industrial process, the acyl D-(+)-carnitinenitrile 2 can be directly converted to L-(−)-carnitine inner salt 6 without isolating either the acyl D-(+)-carnitinamide 3 or the acyl D-(+)-carnitine 4 or the lactone 5.

In fact, the ester of acyl D-(+)-carnitinenitrile 2 is hydrolyzed in an acid environment to compound 3 and this latter to compound 4, then the resulting aqueous solution is concentrated and the concentrate is brought to pH 7–9, preferably 8–9 and kept at this pH value for 30–50 hours yielding L-(−)-carnitine. L-(−)-carnitine thus obtained is purified from any salt via treatment with acidic and basic resins.

In the following example which describes one embodiment of the process of the invention, the intermediate compounds 2, 3 and 4 were isolated so as to exhaustively characterize them from a physico-chemical standpoint.

It will be, however, apparent to any expert in organic synthesis that the industrial process comprises the following steps only:

(a) acylating the hydroxyl group of D-(+)-carnitinenitrile 1 or D-(+)-carnitinamide 1' with an acylating agent RY, wherein R has the previously defined meanings, with the resulting formation of a leaving group OR thus obtaining acyl D-(+)-carnitinenitrile 2 or acyl D-(+)-carnitinamide 3; and (b) converting 2, or respectively 3 to L-(−)-carnitine inner salt 6.

Preparation of methanesulfonyl-D-carnitinenitrile perchlorate 2.

Methanesulfonyl chloride (14.2 g; 123 mmoles) was added over a period of 5 minutes to a solution of D-carnitinenitrile perchlorate 1 (10 g; 41 mmoles) in anhydrous pyridine (200 mL).

The solution was kept under stirring for 1 hour, then poured into an Erlenmeyer flask containing Et$_2$O (800 mL) under stirring. The precipitate which formed was crystallized from hot CH$_3$CN/iPrOH (filtering off the insoluble residue in hot CH$_3$CN).The crystalline product thus obtained was triturated with hot iPrOH yielding 9.4 g of compound 2.

Yield=71% Differential thermal analysis=the compounds melts at 155° C. $[\alpha]_D$=+43°(C=1% H$_2$O)

| TLC = silica gel Eluant = CHCl$_3$/MeOH/iPrOH/H$_2$O/AcOH 42 28 | | | |
|---|---|---|---|
| Rf = 0.58 | 7 | 10.5 | 10.5 |
| Elementary analysis for C$_8$H$_{17}$ClN$_2$O$_7$S | | | |
| | C % | H % | N % | Cl % |
| Calculated | 29.26 | 5.34 | 8.73 | 11.05 |
| Found | 30.21 | 5.35 | 8.47 | 10.97 |

$^1$HNMR(D$_2$O): δ5.78–5.70(m,1H,—CHOMs), 4.12–3.80(m,2H,—CH$_2$N$^+$Me$_3$), 3.42(s,3H,CH$_3$SO$_3$—), 3.42–3.35(m,1H,CHHCOO—),3.30(s,9H,—N$^+$Me$_3$), 3.20–3.12(m,1H,—CHHCOO—) $^{13}$CNMR(D$_2$O): δ118.695; 71.848; 69.616; 57.138; 41.575; 25.965 IR (Kbr)=ν (cm$^{-1}$) 2256 (—C≡N). 1351 and 1175 (CH$_3$SO$_3$—)

HPLC

Column=Nucleosil 5-SA Diameter 4.0 mm Length=200 mm

Eluant=CH$_3$CN/KH$_2$PO$_4$ 50 mM (65/35) pH=3.5 with H$_3$PO$_4$

Flow rate=0.75 mL/min

Retention time=12.80 min.

Detector=RI Waters 410

Preparation of methanesulfonyl D-carnitinamide perchlorate 3.

Methanesulfonyl chloride (9.88 g; 86.31 mmoles) was added over a 5-minute period to a solution of D-carnitinamide perchlorate 1' (15 g; 57.54 mmoles) in anhydrous pyridine (300 mL).

The solution was kept under stirring at room temperature for 1 h and 15 minutes, then poured into an Erlenmeyer flask containing Et$_2$O (2.5 L) under stirring. The precipitate thus obtained was refluxed with iPrOH which was then decanted. The undissolved solid residue was further washed with iPrOH and then dried yielding 10.2 g of compound 3.

Yield=52% Differential thermal analysis =the compound melts at 156°–158° C. $[\alpha]_D^{20}$ =+21.5°(C=1% H$_2$O)

| TLC = silica gel Eluant = CHCl$_3$/MeOH/iPrOH/H$_2$O/AcOH 42 28 | | | | |
|---|---|---|---|---|
| Rf = 0.52 | 7 | 10.5 | 10.5 | |
| Elementary analysis for C$_8$H$_{19}$ClN$_2$O$_8$S | | | | |
| | C % | H % | N % | Cl % | S % |
| Calculated | 28.36 | 5.65 | 8.31 | 10.46 | 9.46 |
| Found | 28.74 | 5.60 | 7.89 | 10.2è | 9.25 |

$^1$HNMR(DMSO)d$_6$): δ7.60 and 7.20(2s,2H,—CONH$_2$), 5.4(m,1H,—CHOMs), 4.0–3.62(4m,2H,—CH$_2$N$^+$Me$_3$), 3.35(s,3H,CH$_3$SO$_3$—)3.15(s,9H,N$^+$Me$_3$), 2.8–2.7(m,2H,—CH$_2$CON) $^{13}$CNMR(D$_2$O): δ175.272; 74.831; 70.798; 56.871; 41.521; 41.308 IR (Kbr)=ν (cm$^-$)1696 (—C=O), 1333 and 1174 (CH$_3$SO$_3$—)

HPLC

Column=Nucleosil 5-SA Diameter 4.0 mm Length=200 mm

Eluant=CH$_3$CN/KH$_2$PO$_4$ 50 mM (65/35) pH=3.5 with H$_3$PO$_4$

Flow rate=0.75 mL/min

Retention time=19.83 min.

Detector=RI Waters 410

Preparation of methanesulfonyl D-carnitine 4 from methanesulfonyl D-carnitinenitrile perchlorate 2.

A solution of methanesulfonyl D-carnitinenitrile perchlorate 2 (2 g; 6.23 mmoles) in 12N HCl (40 mL) was heated at 50° C. under stirring for 36 hours.

The reaction proceeds via the formation of methanesulfonyl-D-carnitinamide 3 as shown by HPLC analysis after 2 hours from reaction beginning.

At the end of the reaction the solution was brought to dryness under vacuum giving an oily solid which was taken up with $CH_3CN$. The insoluble solid was filtered off and the filtrate poured in $Et_2O$; the precipitate thus obtained was isolated by decantation, washed with $Et_2O$ and dried under vacuum yielding 2 g of the raw product 4.
Methanesulfonyl-D-carnitinamide 3.
HPLC Column=Nucleosil 5-SA Diameter 4.0 mm Length=200 mm Eluant=$CH_3CN/KH_2PO_4$ 50 mM (65/35) pH=3.5 with $H_3PO_4$ Flow rate=0.75 mL/min Retention time=19.83 min.

Detector=RI Waters 410

Methanesulfonyl-D-carnitine 4.
HPLC

Column=Nucleosil 5-SA Diameter 4.0 mm Length=200 mm

Eluant=$CH_3CN/KH_2PO_4$ 50 mM (65/35) pH=3.5 with $H_3PO_4$

Flow rate=0.75 mL/min

Retention time=11.38 min.

Detector=RI Waters 410

$^1HNMR(D_2O)$: δ5.70 and 5.6(m,1H,—CHOMs), 4.06–3.75(m,2H,—$CH_2N^+Me_3$ ),3.33(s,3H,$CH_3SO_3$—) 3.27(s,9H,$N^+Me_3$),3.15–3.00(m,2H,—$CH_2COOH$)

The product thus obtained was used as such, without further purification, in the reaction sequence disclosed in the previously cited Italian patent application RM 92 A 000195 to obtain L-carnitine inner salt.
Preparation of methanesulfonyl-D-carnitine 4 from methanesulfonyl-D-carnitinamide perchlorate 3.

The reaction was carried out as described for the reaction starting from methanesulfonyl D-carnitinenitrile perchlorate 2.

We claim:

1. A process for producing L-(−)-carnitine from D-(+)-carnitinenitrile 1 and D-(+)-carnitineamide 1' having the formulas 1 and 1'

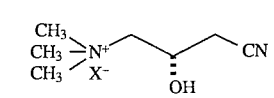

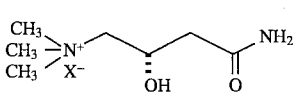

wherein $X^-$ is a counterion, which comprises:

(a) converting 1 or 1' to acyl D-(+)-carnitinenitrile 2 or acyl D-(+)-carnitineamide 3 having the formulas

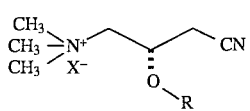

wherein R is selected from the group consisting of $C_1$–$C_{12}$ alkylsulfonyl, formyl, trifluoroacetyl, p-toluenesulfonyl, p-bromobenzenesulfonyl, trifluoromethanesulfonyl, nonafluorobutanesulfonyl, 2,2,2-trifluoroethanesulfonyl, and p-nitrobenzenesulfonyl radicals;

(b) converting the acyl D-(+)-carnitinenitrile 2 or the acyl D-(+)-carnitineamide 3 via acid hydrolysis to acyl D-(+)-carnitine 4 of the formula

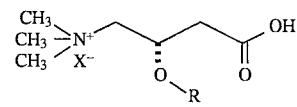

(c) lactonizing the acyl D-(+)-carnitine 4 to the lactone of L-(−)-carnitine 5 of the formula

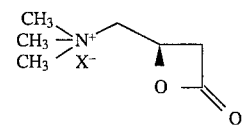

by treating 4 with base; and (d) converting the lactone 5 to L-(−)-carnitine by treating 5 with base.

2. The process of claim 1 wherein, when the precursor is 1, conversion step (a) comprises acylating 1 to produce acyl D-(+)-carnitinenitrile 2 of the formula

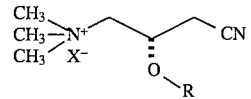

by reacting 1 with an acylating agent RY wherein R is selected from the group consisting of $C_1$–$C_{12}$ alkylsulfonyl, formyl, trifluoroacetyl p-toluenesulfonyl, p-bromobenzenesulfonyl, trifluoromethanesulfonyl, nonafluorobutanesulfonyl, 2,2,2-trifluoroethanesulfonyl, and p-nitrobenzenesulfonyl radicals and Y is halogen in a basic organic or inert anhydrous organic solvent, the acylating agent being added at ratios ranging from 1:1 to 1:10 at 0° C.–50° C., for 1–24 hours.

3. The process of claim 1 wherein, when the precursor is 1', step (a) comprises directly acylating 1' to 3 by reacting 1' with an acylating agent RY wherein R is selected from the group consisting of $C_1$–$C_{12}$ alkylsulfonyl, formyl, trifluoroacetyl p-toluenesulfonyl, p-bromobenzenesulfonyl, trifluoromethanesulfonyl, nonafluorobutanesulfonyl, 2,2,2-trifluoroethanesulfonyl, and p-nitrobenzenesulfonyl radicals and Y is halogen in a basic organic or inert anhydrous organic solvent, the acylating agent being added at ratios ranging from 1:1 to 1:10 at 0° C.–50° C., for 1–24 hours.

4. The process of claim 1, wherein said steps (b), (c) (d) and (e) are carried out as a single step, without isolating said intermediate compounds 2, 3, 4 and 5.

5. The process of claim 1 wherein:

$X^-$ chloride, sulphate, phosphate, perchlorate, metaperiodate, tetraphenylborate, or alkylsulfonate having 1–12 carbon atoms; and R is methanesulfonyl, p-toluenesulfonyl, p-bromobenzenesulfonyl, p-nitrobenzenesulfonyl, trifluoromethanesulfonyl, nonafluorobutanesulfonyl or 2,2,2-trifluoromethanesulfonyl.

6. The process as claimed in claim 1, wherein L-(−)-carnitine is isolated after step (d) by chromatography.

7. The process as claimed in claim 1, wherein $X^-$ is halogenide.

8. The process as claimed in claim 2, wherein Y is chlorine.

9. The process as claimed in claim 2, wherein 1 is reacted with RY in pyridine or a $C_{1-4}$ alkylpyridine.

10. The process as claimed in claim 3, wherein 1' is reacted with RY in pyridine or a $C_{1-4}$ alkylpyridine.

11. The process as claimed in claim 2, wherein said acylating agent is added at a ratio of 1:3.

12. The process as claimed in claim 3, wherein said acylating agent is added at a ratio of 1:3.

13. The process of claim 2, wherein said steps (b), (c), (d) and (e) are carried out as a single step, without isolating intermediate compounds 2, 3, 4 and 5.

14. The process of claim 3, wherein said steps (b), (c), (d) and (e) are carried out as a single step, without isolating intermediate compounds 2, 3, 4 and 5.

15. The process of claim 2, wherein:

$X^-$ is chloride, sulphate, phosphate, perchlorate, metaperiodate, tetraphenylborate, or alkylsulfonate having 1–12 carbon atoms; and R is methanesulfonyl, p-toluenesulfonyl, p-bromobenzenesulfonyl, p-nitrobenzenesulfonyl, trifluoromethanesulfonyl, nonafluorobutanesulfonyl or 2,2,2-trifluoroethanesulfonyl.

16. The process of claim 3, wherein:

$X^-$ is chloride, sulphate, phosphate, perchlorate, metaperiodate, tetraphenylborate, or alkylsulfonate having 1–12 carbon atoms; and R is methanesulfonyl, p-toluenesulfonyl, p-bromobenzenesulfonyl, p-nitrobenzenesulfonyl, trifluoromethanesulfonyl, nonafluorobutanesulfonyl or 2,2,2-trifluoroethanesulfonyl.

17. The process of claim 4, wherein:

$X^-$ is chloride, sulphate, phosphate, perchlorate, metaperiodate, tetraphenylborate, or alkylsulfonate having 1–12 carbon atoms; and R is methanesulfonyl, p-toluenesulfonyl, p-bromobenzenesulfonyl, p-nitrobenzenesulfonyl, trifluoromethanesulfonyl, nonafluorobutanesulfonyl or 2,2,2-trifluoroethanesulfonyl.

18. The process as claimed in claim 1, wherein $X^-$ is chloride and R is mesyl.

19. The process as claimed in claim 1, wherein $X^-$ is halogenide, sulphate, phosphate, perchlorate, metaperiodate, tetraphenylborate, or an alkylsulfonate having 1–12 carbon atoms.

* * * * *

UNITED STATES PATENT AND TRADEMARK OFFICE
CERTIFICATE OF CORRECTION

PATENT NO.   :   5,491,260
DATED        :   February 13, 1996
INVENTOR(S)  :   Fabio GIANNESSI et al.

It is certified that error appears in the above-indentified patent and that said Letters Patent is hereby corrected as shown below:

On the title page and on Column 1, lines 1-4, Item [54] is incorrect. The title should read:

--PROCESS FOR MANUFACTURING L-(-)-CARNITINE FROM CARNITINE DERIVATIVES HAVING A CONFIGURATION OPPOSITE TO THAT OF L-(-)-CARNITINE--

Signed and Sealed this

Eleventh Day of June, 1996

Attest:

BRUCE LEHMAN

Attesting Officer

Commissioner of Patents and Trademarks